(12) United States Patent
Ehrismann et al.

(10) Patent No.: US 7,387,716 B2
(45) Date of Patent: Jun. 17, 2008

(54) POLYMER ELECTROLYTE, HALF CELL FOR ELECTROCHEMICAL MEASUREMENTS, AND THE USE THEREOF

(75) Inventors: Philippe Ehrismann, Uster (CH); Rolf Thrier, Tagelswangen (CH)

(73) Assignee: Mettler-Toledo AG, Greifensee (CH)

( * ) Notice: Subject to any disclaimer, the term of this patent is extended or adjusted under 35 U.S.C. 154(b) by 0 days.

(21) Appl. No.: 11/797,763

(22) Filed: May 7, 2007

(65) Prior Publication Data

US 2007/0205098 A1   Sep. 6, 2007

Related U.S. Application Data

(62) Division of application No. 10/396,401, filed on Mar. 26, 2003, now abandoned.

(30) Foreign Application Priority Data

Mar. 27, 2002  (DE) .................. 102 14 035

(51) Int. Cl.
   *G01N 27/26* (2006.01)
(52) U.S. Cl. .................. 204/433; 204/435; 204/295
(58) Field of Classification Search ............ 204/433, 204/435, 295
   See application file for complete search history.

(56) References Cited

U.S. PATENT DOCUMENTS

| 3,798,750 | A | | 3/1974 | Niedrach |
| 4,432,366 | A | | 2/1984 | Margules |
| 5,436,090 | A | | 7/1995 | Kono et al. |
| 5,549,988 | A | * | 8/1996 | Reichert et al. ............ 429/317 |
| 6,468,408 | B2 | * | 10/2002 | Thrier et al. ............... 204/435 |
| 2002/0193451 | A1 | | 12/2002 | Motonari et al. |
| 2007/0020527 | A1 | * | 1/2007 | Ehrismann et al. ......... 429/314 |

FOREIGN PATENT DOCUMENTS

| DE | 692 12 455 T2 | 3/1997 |
| DE | 693 30 893 T2 | 6/2002 |
| EP | 1 124 132 A1 | 8/2001 |
| WO | WO 93/04360 A1 | 3/1993 |

* cited by examiner

*Primary Examiner*—Bruce F Bell
(74) *Attorney, Agent, or Firm*—Buchanan Ingersoll & Rooney PC

(57) ABSTRACT

A polymer electrolyte for an electrochemical half cell, in particular for a reference half cell, contains a polymer which as a first monomer component contains at least one alkyl methacrylate. The alkyl methacrylate has a substituted alkyl group with from three to seven carbon atoms and at least two substituents. The aforementioned substituents are selected from the group comprising $OR^1$ and $NR^2R^3$, in which $R^1$, $R^2$ and $R^3$ are selected from the group comprising hydrogen, methyl, and ethyl, on the condition that the substituted alkyl group contains the substituent OH at most once.

21 Claims, 1 Drawing Sheet

POLYMER ELECTROLYTE, HALF CELL FOR ELECTROCHEMICAL MEASUREMENTS, AND THE USE THEREOF

RELATED APPLICATIONS

This application is a divisional of prior application Ser. No. 10/396,401, filed Mar. 26, 2003, now abandoned the entire contents of which are hereby incorporated by reference, which in turn claims priority under 35 U.S.C. §119 to German Patent Application No. 10214035.9, filed Mar. 27, 2002, the entire contents of which are hereby incorporated by reference.

BACKGROUND

1. Field of the Invention

The invention relates to a polymer electrolyte, to a half cell, and to uses of the half cell and of the polymer electrolyte.

2. Prior Art

Numerous half cells for electrochemical measurements, such as potentiometric or amperometric measurements, are known. In particular, such half cells can be embodied as reference electrodes, which are used in combination with potentiometric or amperometric sensors. In such reference electrodes, it is important that they output as constant a reference potential as possible.

In one type of reference electrodes, there is a fluid reference electrolyte, such as an aqueous potassium chloride solution, which can be brought into contact with a fluid measuring medium via a liquid connection (also known as a "liquid junction"). To avoid or reduce an unwanted mass transfer between the measuring medium and the reference electrolyte, the liquid junction is typically designed as a more or less porous diaphragm. One disadvantage of such liquid junctions, however, is that soiling or even plugging up of the pores can occur, which can lead to considerable faulty potentials and possibly interruptions.

In another type of reference electrodes, instead of the diaphragm, a single opening or a plurality of openings is provided, as a result of which the aforementioned problem of soiling can be largely avoided. However, this embodiment means that instead of the otherwise usual fluid or gel-like reference electrolyte, a non-flowable reference electrolyte is used, to prevent the reference electrolyte from flowing out. A polymer electrolyte in the form of a hydrogel, which for instance contains a saturated aqueous potassium chloride solution and preferably additionally suspended potassium chloride is especially well suited for this purpose.

In European Patent Disclosure EP 1124132 A1, which is hereby incorporated by reference in its entirety, a reference electrode of this generic type is described which contains a polymer electrolyte that contains a polymer on the basis of monomers selected from N-substituted acrylamides and/or methacrylates. For instance, the methacrylate is a methacrylate with at least two hydroxy groups, and in particular 2,3-dihydroxypropyl methacrylate.

SUMMARY

An object of the invention is to furnish further polymer electrolytes which are especially well suited for electrochemical half cells and in particular for reference half cells. Other objects of the invention are to furnish an improved half cell and to disclose uses of the half cell and of the polymer electrolytes.

The polymer electrolytes of the invention contain a polymer which as a first monomer component contains at least one alkyl methacrylate. The aforementioned alkyl methacrylate has a substituted alkyl group with from three to seven carbon atoms and at least two substituents, and the aforementioned substituents are selected from the group comprising $OR^1$ and $NR^2R^3$, and $R^1$, $R^2$ and $R^3$ are selected from the group comprising hydrogen, methyl, and ethyl, on the condition that the substituted alkyl group contains the substituent OH at most once. By a suitable selection of the substituents in the aforementioned range, the properties of the polymer electrolyte, in particular its polarity and hence its resistance and stability to water or to polar or apolar solvents, can be adapted accordingly to the intended area of use. Moreover, the polymer electrolytes of the invention are distinguished by good resistance and stability to acids.

The half cell of the invention, which can be used as a component in potentiometric or amperometric sensors, contains one of the polymer electrolytes of the invention. The polymer electrolyte of the invention can also be used as a solid-phase electrolyte in a battery half cell.

Exemplary embodiments are directed to the substituted alkyl group of the alkyl methacrylate intended as the first monomer component. According to exemplary embodiments, the substituted alkyl group is a 3-amino-2- hydroxypropyl or a 2-amino-3-hydroxypropyl. Moreover, in accordance in with exemplary embodiments, the substituted alkyl group may be a 3-diethylamino-2-hydroxypropyl, a 3-ethoxy-2-hydroxypropyl, a 3-methoxy-2-hydroxypropyl, or a 3-methylamino-2-hydroxypropyl. Furthermore, according to exemplary embodiments, the substituted alkyl group can be a $-CH_2-CHOH-CH^2-NR^2R^3$ or a $-CH_2-CHNR^2R^3-CH_2OH$, in which $R^2$ and $R^3$, are as described above. Also, the substituted alkyl group can be a $-CH^2-CHOH-CH_2-OR^4$ or a $-CH_2-CHOR^4-CH_2OH$, in which $R^4$ is a methyl or ethyl. However, a mixture of alkyl methacrylates of the type named above can also be contemplated as the first monomer component.

According to exemplary embodiments, the polymer contains, as a further monomer component, a hydroxyalkyl methacrylate, which is preferably 2-hydroxyethyl methacrylate and/or 3-hydroxypropyl methacrylate. With this further monomer component, the polarity of the polymer electrolyte can advantageously be varied, and by a choice of the quantity ratio of the further monomer component to the first monomer component, the polarity is adjustable over a wide range.

Exemplary embodiments can be used in conjunction with a half cell with a glass housing. Because the polymer contains, as an additional monomer component, a silylated alkyl methacrylate, preferably 3-(trimethoxysilyl)propyl methacrylate, an adhesion of the polymer electrolyte to the glass housing is achieved, as a result of which a longer service life of the half cell and in particular better resistance to pressure and washing out is attained.

Exemplary embodiments are directed to a polymer electrolyte. This polymer electrolyte can additionally contain a concentrated aqueous solution of a salt or salt mixture, which is indicated for use in polar measuring media. The polymer electrolyte can contain a mixture of an organic solvent and an aqueous solution of a salt and is accordingly predominantly usable for less-polar measuring media. The organic solvent is selected from the group comprising glycerine, ethylene glycol, methanol, ethanol, N-propanol, isopropanol, acetone, and mixtures thereof. It is especially advantageous if the salt is additionally in the form of a suspension. As a result of the increased salt content, a longer resistance of the half cell to washing out of the salt as a result of the contact with the measuring medium is achieved. On the other hand, the progressive depletion of the salt caused by the washing out can be readily ascertained visually from the developing washing-out or depletion front, which forms the boundary between a region of the polymer electrolyte that is clouded by the salt suspension and a region of the polymer electrolyte that is more clear because the salt suspension is no longer present there. For instance, the aforementioned salt is selected from the group comprising potassium chloride, sodium chloride, lithium chloride, potassium nitrate, potassium perchlorate, sodium formiate, lithium acetate, lithium sulfate, ammonium chloride, methylammonium chloride, dimethylammonium chloride, trimethylammonium chloride, and mixtures thereof. This salt can, however, also be a further ionic organic halide, for instance. This salt can also form a redox system.

The half cell can have an open liquid junction between the polymer electrolyte and a surrounding medium—as a rule, a measuring medium or a fluid specimen. This embodiment is possible because the polymer electrolyte is essentially in solid form and accordingly cannot escape from the open liquid junction. By dispensing with a diaphragm, unwanted interfering potentials in the region of the liquid junction can be largely avoided.

BRIEF DESCRIPTION OF THE DRAWING

The sole drawing figure schematically shows a reference electrode for electrochemical measurements in longitudinal section.

DETAILED DESCRIPTION OF THE PREFERRED EMBODIMENTS

Figure 1:
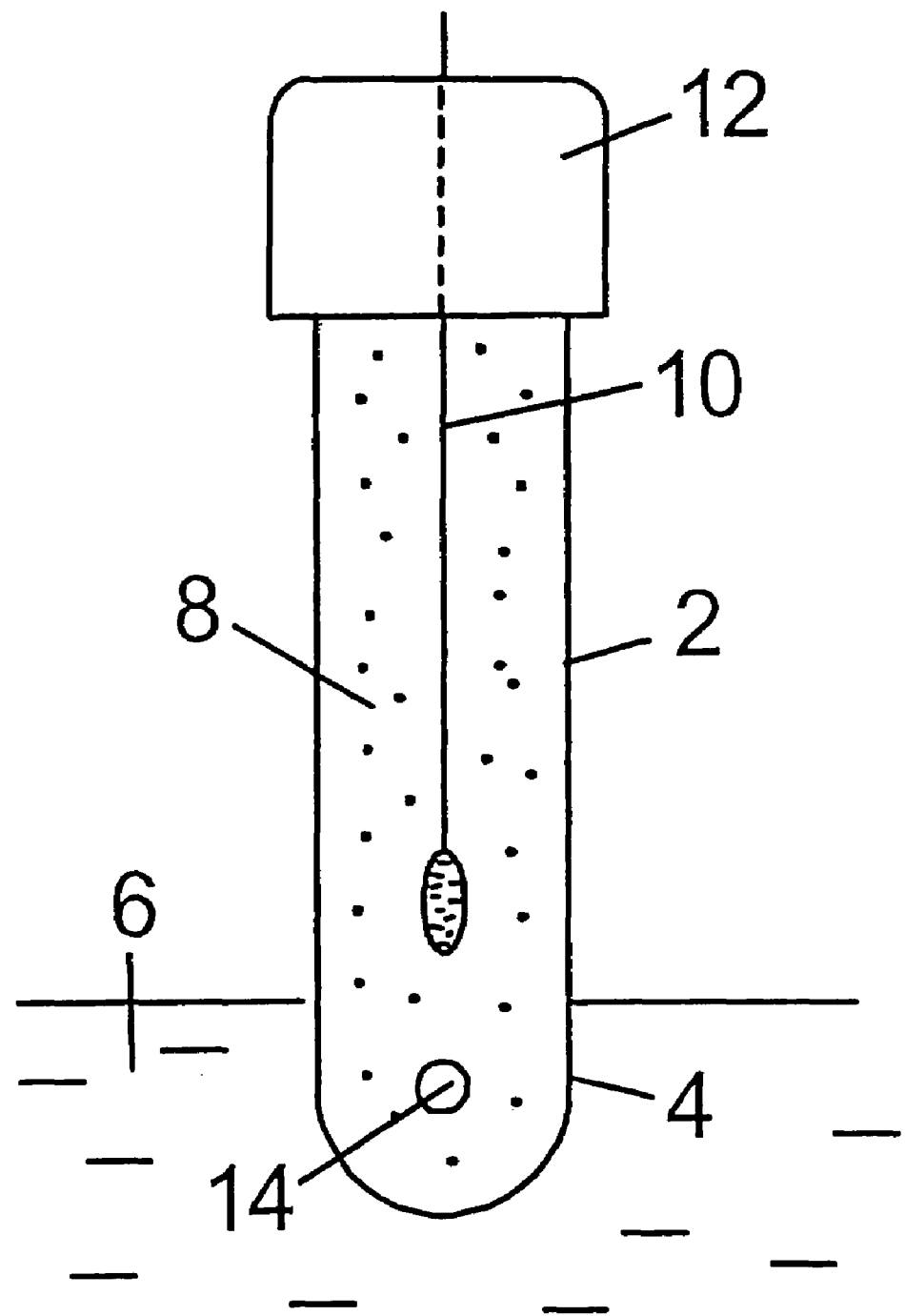

The reference electrode shown in the drawing has a tubular housing 2, made from glass or plastic, whose lower end 4, in the example shown, is immersed in a measuring medium 6. The interior of the housing 2 is filled with a polymer electrolyte 8, in which a lead-off element 10 is immersed. The lead-off element is formed for instance by a chlorinated silver wire, which is extended to the outside through an upper cap part 12 of the housing 2. An opening 14 in the vicinity of the lower end 4 serves as liquid junction between the polymer electrolyte 8 and the measuring medium 6.

The polymer electrolyte 8 is advantageously formed in the interior of the housing 2; first the requisite educts, and in particular the corresponding monomer components, are introduced into the interior, and after that a polymerization is performed. In this reaction, a solidification takes place, so that the polymer electrolyte 8 formed cannot escape from the opening 14.

Besides the reference electrode shown in the drawing, other embodiments are possible. In particular, the reference electrode can be combined with a measuring electrode, for instance a pH electrode, to form a single-rod measurement chain, in a manner known per se. However, still other types of electrochemical half cells can be equipped with the polymer electrolyte, for instance for amperometric measurements. The polymer electrolyte can also be used as a solid-phase electrolyte in a battery half cell.

Production of Preferred Polymer Electrolytes

For producing preferred polymer electrolytes, monomer solutions with a composition shown in Table 1 were mixed with a powder mixture shown in Table 2 and other additives shown in Table 3 and homogenized with cooling at 15 to 20° C. The mixtures thus obtained were introduced into electrodes with a tubular glass housing. By ensuing heat treatment of the filled electrodes, polymerization was initiated, which led to the formation of the polymer electrolytes.

TABLE 1

Monomer Solution

| Substance | Proportion by weight |
|---|---|
| Aminohydroxypropyl methacrylate (AHPMA) | 8 to 12% |
| Hydroxypropyl methacrylate (HPMA) | 4 to 6% |
| Hydroxyethyl methacrylate (HEMA) | 6 to 8% |
| Silylpropyl methacrylate | ca. 0.1% |
| N,N,N',N'-tetramethylethlyenediamine (TEMED) | ca. 0.2% |
| Glycerine | ca. 30% |
| Powder mixture | (according to Table 2) |
| Additives | (according to Table 3) |
| Water | 15 to 20% |

TABLE 2

Powder Mixture

| Substance | Proportion by weight |
|---|---|
| Potassium chloride with 2% aerosil | 25 to 30% |
| Silica gel H60 | 3 to 5% |

TABLE 3

Additives

| Substance | Proportion by weight |
|---|---|
| Methylene-bis-acrylamide (MBA) | ca. 0.5% |
| Ammonium persulfate | ca. 0.05% |
| 2,2'-Azo-bis(2-(2-imidazolin-2-yl)propane) dihydrochloride (WAKO 44) | ca. 0.05% |

The first monomer component, designated above as aminohydroxypropyl methacrylate (AHPMA), is a mixture of the two isomers 3-amino-2-hydroxypropyl methacrylate and 2-amino-3-hydroxypropyl methacrylate, which can be produced for instance by reacting glycidyl methacrylate (2,3-epoxypropyl methacrylate) with ammonia in an isomer ratio of approximately 9:1. WAKO 44 is a radical former that is used as an azo initiator for polymerization reactions. TEMED is a starter compound for the polymerization of acryl and methacryl derivatives. Silica gel and aerosil are used to improve the consistency of the polymer and to adsorb interfering substances, such as electrode poisons, from the measuring medium.

The polymer electrolytes described above are distinguished by excellent stability to acids, water, and both polar and apolar solvents. Accordingly, these polymer electrolytes can be used in the most various types of measuring media.

Further Exemplary Embodiments

For particular areas of use, the properties of the polymer electrolytes can be optimized specifically, as documented by the exemplary embodiments that follow.

TABLE 4

Composition of Example 1

| | Proportion by Weight |
|---|---|
| Monomer | |
| 3-Amino-2-hydroxypropyl methacrylate | 15% |
| 3-(Trimethyloxysilyl)propyl methacrylate | 1% |
| Cross-linking agent | 2% |
| Fillers | |
| KCl | 25% |
| Silicic acid | 5% |
| Solvents | |
| Water | 22% |
| Glycerine | 30% |

TABLE 5

Composition of Example 2

| | Proportion by Weight |
|---|---|
| Monomer | |
| 3-Diethylamino-2-hydroxypropyl methacrylate | 20% |
| 3-(Trimethyloxysilyl)propyl methacrylate | 1% |
| Cross-linking agent | 5% |
| Fillers | |
| KCl | 12% |
| Silicic acid | 8% |
| Solvents | |
| Water | 16% |
| Glycerine | 38% |

TABLE 6

Composition of Example 3

| | Proportion by Weight |
|---|---|
| Monomer | |
| 3-Ethoxy-2-hydroxypropyl methacrylate | 18% |
| 3-(Trimethyloxysilyl)propyl methacrylate | 1% |
| Cross-linking agent | 3% |
| Fillers | |
| KCl | 20% |
| Silicic acid | 5% |
| Solvents | |
| Water | 20% |
| Glycerine | 33% |

TABLE 7

Composition of Example 4

| | Proportion by Weight |
|---|---|
| Monomer | |
| 3-Methoxy-2-hydroxypropyl methacrylate | 19% |
| 3-(Trimethyloxysilyl)propyl methacrylate | 1% |
| Cross-linking agent | 3% |
| Fillers | |
| KCl | 15% |
| Silicic acid | 6% |
| Solvents | |
| Water | 21% |
| Glycerine | 35% |

TABLE 8

Composition of Example 5

| | Proportion by Weight |
|---|---|
| Monomer | |
| 3-Methylamino-2-hydroxypropyl methacrylate | 14% |
| 3-(Trimethyloxysilyl)propyl methacrylate | 1% |
| Hydroxypropyl methacrylate | 4% |
| Cross-linking agent | 5% |
| Fillers | |
| KCl | 20% |
| Silicic acid | 5% |
| Solvents | |
| Water | 15% |
| Glycerine | 36% |

All the polymer electrolytes described above here have good stability to acids; other properties are listed in Table 9.

TABLE 9

Properties of the Polymer Electrolytes Investigated

| Example | Polarity | Area of Use | KCl Solution |
|---|---|---|---|
| 1 | Strong | Water; no organic solvents | Supersaturated |
| 2 | Medium-strong | Water; polar organic solvents | Supersaturated |
| 3 | Very weak | Apolar organic solvents | Supersaturated |
| 4 | Medium-weak | Polar organic solvents | Saturated |
| 5 | Weak | Polar and apolar organic solvents | Supersaturated |

Individually, the following properties were also ascertained. The polymer electrolyte of Example 1 is stable to water but not to organic solvents. The polymer electrolyte of Example 2 is suitable for use with water and polar solvents. The polymer electrolyte of Example 4, compared to that of Example 3, has a shorter service life. The polymer electrolyte of Example 5 is especially well suited, because of its stability, for use with any organic solvents.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced thereon.

What is claimed is:

1. An electrochemical half cell, comprising:
   a housing suitable for immersion into a measuring medium, wherein the interior of the housing contains a polymer electrolyte,
   wherein the polymer electrolyte comprises a polymer which as a first monomer component contains at least one alkyl methacrylate, wherein the alkyl methacrylate has a substituted alkyl group with from three to seven carbon atoms and at least two substituents, and the substituents are selected from the group consisting of $OR^1$ and $NR^2R^3$, and $R^1$, $R^2$ and $R^3$ are selected from the group consisting of hydrogen, methyl, and ethyl, on a condition that the substituted alkyl group contains at least one $NR^2R^3$ substituent, and a substituent OH at most once.

2. The electrochemical half cell of claim 1, wherein the substituted alkyl group is a 3-amino-2-hydroxypropyl.

3. The electrochemical half cell of claim 1, wherein the substituted alkyl group is a 2-amino-3-hydroxypropyl.

4. The electrochemical half cell of claim 1, wherein the substituted alkyl group is a 3-diethylamino-2-hydroxypropyl.

5. The electrochemical half cell of claim 1, wherein the substituted alkyl group is a 3-ethoxy-2-hydroxypropyl.

6. The electrochemical half cell of claim 1, wherein the substituted alkyl group is a 3-methoxy-2-hydroxypropyl.

7. The electrochemical half cell of claim 1, wherein the substituted alkyl group is a 3-methylamino-2-hydroxypropyl.

8. The electrochemical half cell of claim 1, wherein the substituted alkyl group is a $—CH_2—CHOH—CH_2—NR^2R^3$ or a $—CH_2—CHNR^2R^3—CH_2OH$, in which $R^2$ and $R^3$ are as defined in claim 1.

9. The electrochemical half cell of claim 1, wherein the substituted alkyl group is a $—CH_2—CHOH—CH_2—OR^4$ or a $—CH_2—CHOR^4—CH_2OH$, in which $R^4$ is a methyl or ethyl.

10. The electrochemical half cell of claim 1, wherein the polymer contains, as a further monomer component, a hydroxyalkyl methacrylate.

11. The electro chemical half cell of claim 1, wherein the polymer contains, as an additional monomer component, a silylated alkyl methacrylate, preferably 3-(trimethoxysilyl) propyl methacrylate.

12. The electrochemical half cell of claim 1, wherein it additionally contains a concentrated aqueous solution of a salt or salt mixture.

13. The electrochemical half cell of claim 1, wherein it additionally contains a mixture of an organic solvent and an aqueous solution of a salt.

14. The electrochemical half cell of claim 13, wherein the organic solvent is selected from the group consisting of glycerine, ethylene glycol, methanol, ethanol, N-propanol, isopropanol, acetone, and mixtures thereof.

15. The electrochemical half cell of claim 12, wherein the salt is in the form of a suspension.

16. The electrochemical half cell of claim 12, wherein the salt is selected from the group consisting of potassium chloride, sodium chloride, lithium chloride, potassium nitrate, potassium perchlorate, sodium formiate, lithium acetate, lithium sulfate, ammonium chloride, methylammonium chloride, dimethylammonium chloride, trimethylammonium chloride, and mixtures thereof.

17. The electrochemical half cell of claim 1, comprising: an open liquid junction between the polymer electrolyte and a surrounding medium.

18. A potentiometric or amperometric sensor, comprising the electrochemical half cell of claim 1.

19. A battery half cell, comprising the electrochemical half cell of claim 1, wherein the polymer electrolyte is a solid-phase electrolyte.

20. An electrochemical half cell, comprising:
    a housing suitable for immersion into a measuring medium, wherein the interior of the housing contains a polymer electrolyte,
    wherein the polymer electrolyte comprises a polymer which as a first monomer component contains at least one alkyl methacrylate, wherein the alkyl methacrylate has a substituted alkyl group with from three to seven carbon atoms and at least two substituents, and the substituents are selected from the group consisting of $OR^1$ and $NR^2R^3$, and $R^1$, $R^2$ and $R^3$ are selected from the group consisting of hydrogen, methyl, and ethyl, on a condition that the substituted alkyl group contains at least one $NR^2R^3$ substituent, and a substituent OH at most once,
    wherein the electrochemical half cell is a reference half cell.

21. The electrochemical half cell of claim 1, wherein the polymer contains, as a further monomer component, a 2-hydroxyethyl methacrylate and/or 3-hydroxypropyl methacrylate.

* * * * *